US006420182B1

(12) United States Patent
Start

(10) Patent No.: US 6,420,182 B1
(45) Date of Patent: Jul. 16, 2002

(54) PRENATAL GENDER PREDICTION TEST

(75) Inventor: Steven Booth Start, Dalkeith (CA)

(73) Assignee: Mediel Establishment, Triesenberg (LI)

( * ) Notice: Subject to any disclaimer, the term of this patent is extended or adjusted under 35 U.S.C. 154(b) by 0 days.

(21) Appl. No.: 09/334,733

(22) Filed: Jun. 17, 1999

(51) Int. Cl.$^7$ ................................................ G01N 31/16
(52) U.S. Cl. ........................ 436/163; 436/164; 436/814; 436/183; 436/65; 600/309
(58) Field of Search ................................. 436/163, 164, 436/814, 183, 65; 600/309

(56) References Cited

U.S. PATENT DOCUMENTS

| | | | |
|---|---|---|---|
| 4,358,535 A | | 11/1982 | Falkow et al. .................. 435/5 |
| 4,731,332 A | * | 3/1988 | Blumenthal et al. .......... 436/61 |
| 4,840,914 A | | 6/1989 | Weisberg .................... 436/183 |
| 5,753,451 A | * | 5/1998 | Smith .......................... 435/12 |

OTHER PUBLICATIONS

Lagona, F. et al., "Multiple testing in fetal gender determination from maternal blood by polymerase chain reaction", *Hum Genet*, vol. 102, No. 6, 1 page (Jun. 1998).

Olsen, A. et al., "Isolation of Unique Sequence Human X Chromosomal Deoxyribonucleic Acid", *Biochemistry*, vol. 19, No. 11, pp. 2419–2428 (May 27, 1980).

Takabayashi, H. et al., "Development of non–invasive fetal DNA diagnosis from maternal blood", *Prenat Diagn*, vol. 15, No. 1, 1 page (Jan. 1995).

Willard, H. et al., "Isolation and characterization of a major tandem repeat family from the human X chromosome", *Nucleic Acids Research*, vol. 11, No. 7, pp. 2017–2033 (Apr. 11, 1983).

* cited by examiner

*Primary Examiner*—Jill Warden
*Assistant Examiner*—Monique T Cole
(74) *Attorney, Agent, or Firm*—Merchant & Gould P.C.

(57) ABSTRACT

The present invention provides a gender-indicating composition, and a method and kit for determining the gender of an unborn child. The gender-indicating composition includes thymol blue and can be in solid or solution form. The method of the invention includes a non-invasive colorimetric assay of a pregnant woman's urine. The kit includes a unit dose of the gender-indicating composition and, optionally, a color standard.

10 Claims, No Drawings

PRENATAL GENDER PREDICTION TEST

BACKGROUND

Prospective parents are often very interested in knowing the sex of their unborn child. While there are many methods for attempting to determine the gender of an unborn child, many of the methods are based on folklore rather than scientific principles. The accuracy of such techniques is doubtful. Scientifically based techniques are also available for attempting to determine the gender of an unborn child. However, many of the scientific techniques for determining the gender of an unborn baby are either invasive of the mother, the womb or the fetus or require expensive equipment. Amniocentesis involves insertion of a cannula or needle into the amniotic sac. Ultrasonographic examination of the fetal perineal can be used to attempt to detect external genitalia of a male fetus. However, ultrasound requires expensive equipment and has not proven to be completely reliable. Several approaches based on changes in the mother's endocrinology have been explored. For example, attempts to examine hormone levels in pregnant mothers have not resulted in any statistically reliable methods for distinguishing between mothers carrying a male fetus versus mothers carrying a female fetus. Other tests, such as polymerase chain reaction (PCR) amplification of Y-specific DNA sequences in maternal blood, require a sample of maternal blood and expensive equipment.

It would accordingly be very desirable to have a simple, reliable non-invasive method for determining the gender of an unborn baby.

SUMMARY

The present invention provides a gender-indicating composition, and a method and kit for determining the gender of an unborn child. The gender-indicating composition includes thymol blue and may include one or more additional indicators as discussed below. The gender-indicating composition can be provided in any of a number of common forms. For example, gender-indicating composition may be in the form of a powder or a solution which includes a water miscible organic solvent. One particularly suitable form of the gender-indicating composition is an aqueous solution that includes a water-miscible organic solvent, such as a water-miscible alcohol. Suitable examples of water-miscible alcohols include ethanol and methanol. The gender-indicating composition optionally may also include non-interfering indicators such as bromthymol blue, phenolphthalin or methyl red.

The present invention also provides a non-invasive colorimetric assay of a pregnant woman's urine to determine the sex of the fetus. According to the present method, the gender-indicating composition is combined with a urine sample from a pregnant woman. The resulting treated urine solution is generally compared to a color standard.

The present invention also provides a kit for assaying a pregnant woman's urine to determine the sex of the fetus. The kit includes a dosage unit of the gender-indicating composition. The kit may also includes a color standard to which the color of the treated urine solution is compared. Typically, the color standard includes a male child color standard and/or a female child color standard. Optionally, the kit can include instructions for performing the colorimetric assay and/or a reaction vessel in which the assay can be performed.

DETAILED DESCRIPTION

The present invention provides a gender-indicating composition, method and kit for determining the gender of an unborn child.

Gender-Indicating Composition

One aspect of the invention provides a gender-indicating composition. According to the invention, the gender-indicating composition includes thymol blue. Optionally, the gender-indicating composition can include non-interfering indicators such as bromthymol blue, phenolphthalin, methyl red or mixtures thereof. As used herein, the term "non-interfering" indicators refers to colorimetric indicators which do not affect the color of the treated urine solution under the test conditions. Suitable "non-interfering" indicators are preferably uncolored or yellow in their acid form (e.g., at a pH of about 1–7) and uncolored or yellow in their base form (e.g., at a pH of 7–14). The color response of a number of common pH indicators are shown in Table 1, below.

In some instances the presence of the optional non-interfering indicator(s) can have an advantageous effect. For example, the presence of bromthymol blue and phenolphthalin can enhance the stability of test solutions containing thymol blue. Although the bromthymol blue and phenolphthalin are not necessary components of the indicator solution, their action can occupy varying pH levels of the buffer offering color consistency for the indicators. Weak acid and weak bases are often found in urine, which regularly has high concentrations of both. The levels can vary depending on a person's diet. Adding an equal number of moles (for example, equal volumes of solutions of the same molarity) of each will result in a neutral solution. Adding more acid will result in an acidic solution. Conversely, adding more base will result in a basic solution. The bromthymol blue and phenolphthalin occupy the pH around neutrality, thus providing a more suitable buffer to conduct the present gender test.

TABLE 1

Known pH Indicators

| Indicator | pH range | pKa | Acid Form | Base Form |
| --- | --- | --- | --- | --- |
| thymol blue | 1.2–2.8 | 1.6 | red | yellow |
| methyl red | 4.2–6.2 | 5.0 | red | yellow |
| bromthymol blue | 6.0–7.6 | 7.1 | yellow | blue |
| thymol blue | 8.0–9.6 | 8.9 | yellow | blue |
| phenolphthalin | 8.0–9.8 | 9.7 | colorless | red |

The present gender-indicating composition can be in the form of a solid, e.g., crystals or a powder. Alternatively, the gender-indicating composition combined with a neutral water miscible organic solvent to form a gender-indicating solution. The gender-indicating solution may be a relatively dilute form of the gender-indicating composition such that 1 to 10 mL of the solution are combined with a urine sample (e.g., circa 50–100 mL of urine) during the test. Alternatively, the gender-indicating solution may be a relatively concentrated solution of the gender-indicating composition such that only a few drops of the solution are needed to conduct the test on an urine sample of 50 mL or larger. The amount of polypeptide byproduct to be detected which is dissolved in the test solution may be of a very low concentration, and the thymol blue, a necessary component, indicates specific to the gender test.

As discussed above, gender-indicating composition includes thymol blue and may include one or more additional indicators. Thymol blue (4,4'-(3H-2, 1-Benzoxathiol-3-ylidene)bis[5-methyl-2-(1-methylethyl)phenol] S,S-dioxide) is a known acid-base indicator. Thymol blue reported to be a brown/green powder or crystalline material that is soluble in alcohol or dilute alkali. As indicated in Table 1, at a pH of 1.2 thymol blue is red; at a pH between 2.8 and 8.0, thymol blue is yellow; and at a pH of 9.6 or above, this indcator is blue.

The present gender-indicating composition commonly also includes bromthymol blue in addition to the thymol blue. Bromthymol blue is 4,4'-(3H-2,1-Benzoxathiol-3-ylidene)bis[2-bromo-3-methyl-6-(1-methylethyl)phenol] S,S-dioxide. Bromthymol blue is reported to exist as cream colored crystals and be sparingly soluble in water, soluble is alcohol or ether and aqueous solutions of alkali. As indicated in Table 1, at a pH of 6.0 bromthymol blue is yellow and at a pH of 7.6 bromthymol is blue.

Other indicators which may be present gender-indicating composition include methyl red and/or phenolphthalin. Methyl red (2-[[4-(Dimethylamino)phenyl]azo]-benzoic acid) is a known acid-base indicator. Methyl red is a dark-red powder or a violet crystalline material. It is reported to be soluble in alcohol, ether, and glacial acetic acid. Typically, methyl red is prepared in an alcoholic solution, for example, a 0.1% aqueous alcoholic solution. At a pH of 4.4 or below, methyl red is red. At a pH of 6.2 methyl red is yellow.

In test solutions, the function of methyl red can be defined as having the capacity to minimize changes in the sought after pH, 2.5. The methyl red can become part of a highly conjugated system that can allow more electrons to be delocalized resulting in smaller energy gaps between the thymol blue indicator and the polypeptide byproduct which is detected in the test solution, so excitation requires less energy resulting in absorption in the visible region. This can produce a broadening of the sensitivity of the test. In other words, the presence of the methyl red can create a pH specific biased buffer solution which contains a weak acid and its conjugate weak base at comparable formal concentrations. The ration of formal acid and base concentrations is the most important criterion of the buffer action.

Phenolphthalin (2-[Bis(4-hydroxyphenyl)methyl]-benzoic acid) is a known acid-base indicator. Phenolphthalin is a pale yellow powder that is soluble in alcohol, ether and alkalis. Phenolphthalin is pink to deep red in the presence of alkali, but colorless in the presence of large amounts of alkali. Phenolphthalin is colorless below a pH of 8.0 and red at pH 9.8.

According to the invention, the gender-indicating composition can be used as a solid or powder or the gender-indicating composition can be combined with a solvent to form a gender-indicating composition. Suitable solvents include neutral water-miscible organic solvents in which the indicators are soluble. As used herein, the term "neutral" refers to a solvent which does not impact the acid/base equivalence of the treated urine solution, i.e., addition of the solvent does not substantially alter the pH. Examples of non-neutral solvents include organic acids ($RCO_2H$) and amines ($R_3N$). Examples of suitable neutral solvents include alcohol, such as methanol, ethanol and isopropanol; dimethylformamide; dimethylacetamide; dimethylsulfoxide; acetone; methyl ethyl ketone; ethylene glycol; n-methyl pyrrolidone and acetonitrile. Preferably, the solvent includes alcohol, such as methanol or ethanol. More preferably, the solvent includes methanol.

The indicator can be combined with the solvent to form either a concentrated solution or a dilute solution. Generally, the solution should include an amount of gender-indicating composition sufficient to provide a reliable color change when combined with a pregnant woman's urine sample. A dilute gender-indicating solution that includes less gender-indicating composition will generally provide a weaker color intensity than an equal amount of a concentrated gender-indicating solution. If more intense color is desired, a larger quantity of the dilute solution can be added to the urine sample. As used herein, a "concentrated solution" includes about 1 ppm to about 50 ppm thymol blue; and optionally, about 0.5 ppm to about 25 ppm methyl red, about 1 ppm to about 50 ppm bromthymol blue, and/or about 0.25 ppm to about 15 ppm phenolphthalin. More preferably, a concentrated solution includes about 1 ppm to about 10 ppm thymol blue; and may also include about 0.5 ppm to about 5 ppm methyl red, about 1 ppm to about 10 ppm bromthymol blue, and/or about 0.25 ppm to about 2.5 ppm phenolphthalin. A "dilute solution" includes about 0.1 ppm to about 1 ppm thymol blue; and optionally about 0.05 ppm to about 0.5 ppm methyl red, about 0.1 ppm to about 1 ppm bromthymol blue, and/or about 0.025 ppm to about 0.25 ppm phenolphthalin. More preferably the "dilute solution" includes about 0.5 ppm to about 1 ppm thymol blue; and optionally about 0.25 ppm to about 0.5 ppm methyl red, about 0.5 ppm to about 1 ppm thymol blue, and/or about 0.1 ppm to about 0.25 ppm phenolphthalin.

Generally, the intensity of the color change is related to the concentration of the gender-indicating composition in the treated urine solution. The concentration in the treated urine solution is typically about 0.02 ppm to about 0.06 ppm thymol blue; and optionally, about 0.01 ppm to 0.03 ppm methyl red, about 0.02 ppm to about 0.06 ppm bromthymol blue, and/or about 0.005 ppm to about 0.015 ppm phenolphthalin.

Method

Another aspect of the invention is directed towards a method for determining the gender of an unborn child. According to the invention, the gender-indicating composition is combined with a urine sample from a woman pregnant with the unborn child to form a treated urine solution. The resulting treated urine solution is compared with a color standard. Typically, the color standard includes at least one of a male child standard, a female child standard and a non-pregnant standard. Preferably, the color standard includes at least a male child standard and a female child standard. According to the invention, the male child color standard is a red or orange color, or a combination of both, and the female child color standard is a green or blue, or a combination of both.

The gender-indicating composition can be combined with the urine sample as a powder, a concentrated solution, or a dilute solution. The amount and concentration of the gender-indicating solution added to the urine sample may affect the color intensity of the treated urine solution. Generally, the gender-indicating solution should include an amount of gender-indicating composition sufficient to provide a reliable color change when combined with a pregnant woman's urine sample. Generally, a dilute gender-indicating solution that includes less gender-indicating composition will provide a weaker color than an equal amount of a concentrated indicator. If more intense color is desired, a larger quantity of the dilute gender-indicating solution can be added to the urine sample. For example, about 0.1 mL to about 1 mL of a concentrated gender-indicating solution can be combined with about 50 mL to about 100 mL of a urine sample. Alternately, about 1 mL to about 10 mL of a dilute gender-indicating solution can be combined with about 50 mL to about 100 mL of a urine sample.

After the gender-indicating composition is combined with the urine sample, the color of the resulting treated urine solution is compared with a color standard. To reduce the likelihood of a false result due to color attenuation, it is preferred that the treated urine solution is compared with a color standard about 1 minute to about 30 minutes, more preferably about 5 minutes to about 10 minutes, after the gender-indicating composition is added.

Kit

The present invention also provides a kit for determining the gender of an unborn child. According to the invention, the kit includes a dosage unit of a gender-indicating composition. Optionally, the kit may also include a color standard to which the color of the treated urine solution can be compared. The gender-indicating composition can be a solid or powder or combined with a solvent to form a gender-indicating solution. As used herein, "unit dose" refers to an amount of a gender-indicating composition sufficient to carry out the gender-determining calorimetric assay on a single urine sample. Typically, the amount of gender-indicating composition in a unit dose is based on the amount of the composition which is sufficient to carry out the fetal sex determination on a urine sample having a predetermined volume. Preferably, the amount of gender-indicating composition is sufficient to give a reliable color change to indicate the gender of an unborn child. The urine sample commonly has a volume from about 10 mL to about 200 mL and, preferably, from about 75 mL to about 100 mL. The critical feature is the amount of gender-indicating component(s) present and not the overall volume of the composition. For example, the volume of the "unit dose" varies depending on whether the gender-indicating composition is a powder, a dilute solution or a concentrated solution. Examples of a suitable "unit dose" are 0.1 mL to 1 mL concentrated solutions of the gender-indicating component(s). Alternately, a suitable "unit dose" can be about 1 mL to about 10 mL of a dilute gender-indicating solution. Or, a suitable "unit dose" can be about 0.1 mg to about 1 mg of a solid gender-indicating composition.

Optionally, the kit can included instructions for performing the calorimetric assay and/or a reaction vessel for performing the assay.

WORKING EXAMPLES

Example 1

Preparation of Gender-indicating Composition

One example of an illustrative gender-indicating composition was prepared by dissolving the quantities of indicators shown below in Table 2 in 20 gallons of laboratory grade methanol.

TABLE 2

Gender-indicating composition

| Indicator | Grade | Quantity | Concentration |
| --- | --- | --- | --- |
| Methyl Red | Reagent A.C.S. | 30.3 grams | 0.505 ppm |
| Bromthymol Blue | Reagent A.C.S. | 60.6 grams | 1.01 ppm |
| Thymol Blue | Reagent A.C.S. | 75.8 grams | 1.26 ppm |
| Phenolphthalin | Laboratory Grade Powder | 15.1 grams | 0.25 ppm |
| Methanol | Laboratory Grade | 20.0 gal | — |

Example 2

Determining Gender of Unborn Child

In this example, the gender of unborn children of 103 pregnant women were determined using the gender-indicating composition of Example 1 and the following protocol: 60–70 cc of urine was collected from each pregnant woman and placed in a be -glass reaction vessel. The gender-indicating composition was added to the urine sample. After agitating the mixture, the color of the treated urine solution was observed. A subtle yellow or strong green indicated the unborn child was female. A orange-red color indicated the unborn child was male.

The assay was performed at weeks 12, 14, 16, 18, 20 and 22 of pregnancy. In most instances, the gender of the unborn child was also determined using ultrasound. The results of the calorimetric assay and the ultrasound determination of gender were then compared to the actual gender of the child observed at birth. The colorimetric assay provided 100% accuracy out of 103 patients. In contrast, ultrasound was accurate in 43 out of the 46 births (94%) for which an ultrasound determination was reported.

TABLE 3

Results of gender-determining assay

| Subject No. | E.D.D.* | A.D.D.+ | Wk 12 | Wk 14 | Wk 16 | Wk 18 | Wk 20 | Wk 22 | Ultra Sound | Actual |
| --- | --- | --- | --- | --- | --- | --- | --- | --- | --- | --- |
| 1. | Dec 20 | Dec 11 | M | M | M | M | M | M | N/A | M |
| 2. | Dec 3 | Nov 28 | F | F | F | F | F | F | F | F |
| 3. | Dec 15 | Dec 24 | M | M | M | M | M | M | N/A | M |
| 4. | Dec 12 | Dec 14 | M | M | M | M | M | M | M | M |
| 5. | Jan 5 | Jan 5 | F | M | M | M | M | M | M | M |
| 6. | Jan 3 | Dec 26 | F | F | F | F | F | F | N/A | F |
| 7. | Jan 7 | Jan 14 | M | M | M | M | M | M | N/A | M |
| 8. | Feb 1 | Jan 22 | F | F | F | F | F | F | F | F |
| 9. | Nov 22 | Nov 24 | F | F | F | F | F | F | F | F |
| 10. | Dec 16 | Dec 17 | F | F | F | F | F | F | N/A | F |
| 11. | Dec 25 | Dec 30 | M | M | M | M | M | M | M | M |
| 12. | Feb 2 | Feb 4 | F | F | F | F | F | F | F | F |
| 13. | Jan 18 | Jan 11 | F | F | F | F | F | F | N/A | F |
| 14. | Feb 12 | Jan 15 | M | M | M | M | M | M | N/A | M |
| 15. | Apr 9 | Apr 10 | F | F | F | F | F | F | N/A | F |
| 16. | Mar 15 | Mar 22 | F | F | F | F | F | F | N/A | F |
| 17. | May 10 | Apr 26 | F | F | F | F | F | F | N/A | F |
| 18. | Apr 21 | May 15 | M | M | M | M | M | M | M | M |
| 19. | Apr 9 | Apr 22 | F | F | F | F | F | F | N/A | F |
| 20. | Apr 14 | Apr 15 | F | M | M | M | M | M | M | M |
| 21. | May 17 | May 17 | F | F | F | F | F | F | F | F |

TABLE 3-continued

Results of gender-determining assay

| Subject No. | E.D.D.* | A.D.D.+ | Wk 12 | Wk 14 | Wk 16 | Wk 18 | Wk 20 | Wk 22 | Ultra Sound | Actual |
|---|---|---|---|---|---|---|---|---|---|---|
| 22. | Jun 27 | Jun 27 | F | F | F | F | F | F | N/A | F |
| 23. | Jun 2 | May 25 | F | M | M | M | M | M | M | M |
| 24. | Jun 7 | Jun 14 | F | F | F | F | F | F | F | F |
| 25. | Jun 12 | Jun 12 | M | M | M | M | M | M | N/A | M |
| 26. | Jun 8 | Jun 12 | M | M | M | M | M | M | F | M |
| 27. | Apr 21 | May 1 | F | F | F | F | F | F | F | F |
| 28. | May 16 | May 12 | F | F | F | F | F | F | N/A | F |
| 29. | Apr 21 | Mar 27 | F | M | M | M | M | M | M | M |
| 30. | Jun 11 | Jun 12 | F | F | F | F | F | F | F | F |
| 31. | Jun 9 | Jun 14 | M | M | M | M | M | M | N/A | M |
| 32. | Jun 2 | Jun 20 | M | M | M | M | M | M | M | M |
| 33. | Apr 16 | Apr 13 | F | F | F | F | F | F | F | F |
| 34. | Mar 27 | Mar 21 | F | F | F | F | F | F | N/A | F |
| 35. | Jun 12 | Jun 16 | F | F | F | F | F | F | N/A | F |
| 36. | Jun 17 | Jun 23 | F | F | F | F | F | F | N/A | F |
| 37. | Jun 2 | Jun 9 | M | M | M | M | M | M | N/A | M |
| 38. | Apr 15 | Apr 5 | M | M | M | M | M | M | M | M |
| 39. | Jun 22 | Jun 15 | F | M | M | M | M | M | M | M |
| 40. | May 5 | May 9 | F | F | F | F | F | F | N/A | F |
| 41. | Jul 3 | Jun 26 | F | F | F | F | F | F | F | F |
| 42. | Jun 7 | Jun 11 | M | M | M | M | M | M | M | M |
| 43. | Jun 2 |  | F | F | F | N/A | N/A | N/A | N/A | N/A |
| 44. | Jun 9 | Jun 10 | F | F | F | F | F | F | N/A | F |
| 45. | Jun 12 | Jun 18 | M | M | M | M | M | M | N/A | M |
| 46. | Jul 12 | Jul 18 | F | F | F | F | F | F | F | F |
| 47. | Aug 21 | Sep 3 | F | F | F | F | F | F | F | F |
| 48. | Aug 15 | Aug 19 | M | M | M | M | M | M | M | M |
| 49. | Sep 19 | Sep 18 | M | M | M | M | M | M | M | M |
| 50. | Sep 22 | Sep 11 | F | F | F | F | F | F | F | F |
| 51. | Sep 15 | Sep 18 | F | F | F | F | F | F | F | F |
| 52. | Aug 30 | Sep 1 | F | M | M | M | M | M | M | M |
| 53. | Oct 5 | Sep 29 | M | M | M | M | M | M | M | M |
| 54. | Sep 17 | Sep 10 | F | F | F | F | F | F | F | F |
| 55. | Oct 12 | Oct 17 | F | M | M | M | M | M | M | M |
| 56. | Oct 5 | Oct 16 | F | F | F | F | F | F | F | F |
| 57. | Oct 17 | Oct 20 | F | M | M | M | M | M | M | M |
| 58. | Nov 11 | Nov 28 | F | F | F | F | F | F | N/A | F |
| 59. | Sep 26 | Oct 4 | F | F | F | F | F | F | M | F |
| 60. | Nov 2 | Nov 16 | F | F | F | F | F | F | N/A | F |
| 61. | Oct 21 | Oct 16 | F | F | F | F | F | F | N/A | F |
| 62. | Aug 21 | Aug 25 | M | M | M | M | M | M | N/A | M |
| 63. | Aug 15 | Aug 10 | F | M | M | M | M | M | N/A | M |
| 64. | Oct 11 |  | F |  |  |  |  |  | N/A | N/A |
| 65. | Nov 24 | Dec 3 | F | F | F | F | F | F | N/A | F |
| 66. | Sep 12 |  | F |  |  |  |  |  | Multiple |  |
| 67. | Sep 19 | Sep 1 | F | M | M | M | M | M | M | M |
| 68. | Aug 6 | Aug 9 | M | M | M | M | M | M | N/A | M |
| 69. | Oct 18 | Oct 10 | F | F | F | F | F | F | F | F |
| 70. | Nov 14 | Nov 21 | F | F | F | F | F | F | N/A | F |
| 71. | Oct 22 | Nov 1 | F | F | F | F | F | F | N/A | F |
| 72. | Aug 22 | Aug 10 | F | F | F | F | F | F | N/A | M |
| 73. | Nov 5 | Nov 10 | F | F | F | F | F | F | N/A | F |
| 74. | Sep 11 | Sep 18 | M | M | M | M | M | M | M | M |
| 75. | Oct 29 | Nov 5 | F | F | F | F | F | F | N/A | F |
| 76. | Jan 6 | Dec 27 | M | M | M | M | M | M | N/A | M |
| 77. | Nov 15 | Nov 9 | F | F | F | F | F | F | N/A | F |
| 78. | Dec 7 | Dec 11 | F | F | F | F | F | F | N/A | F |
| 79. | Jan 17 | Jan 10 | F | F | F | F | F | F | F | F |
| 80. | Nov 12 | Nov 13 | M | M | M | M | M | M | N/A | M |
| 81. | Oct 21 | Oct 29 | F | F | F | F | F | F | N/A | F |
| 82. | Dec 7 | Nov 28 | F | F | F | F | F | F | F | F |
| 83. | Feb 19 | Feb 17 | F | F | F | F | F | F | N/A | F |
| 84. | Oct 2 | Sep 20 | F | F | F | F | F | F | N/A | F |
| 85. | Dec 28 | Dec 25 | F | F | F | F | F | F | N/A | F |
| 86. | Mar 16 | Mar 26 | F | F | F | F | F | F | F | F |
| 87. | Jan 5 | Jan 12 | F | F | F | F | F | F | N/A | F |
| 88. | Feb 23 | Feb 19 | F | F | F | F | F | F | N/A | F |
| 89. | Jan 11 | Jan 20 | F | F | F | F | F | F | N/A | F |
| 90. | Feb 18 | Feb 9 | M | M | M | M | M | M | M | M |
| 91. | Mar 3 | Feb 26 | M | M | M | M | M | M | N/A | M |
| 92. | Feb 9 | Feb 18 | F | F | F | F | F | F | F | F |
| 93. | Jan 15 | Jan 9 | F | F | F | F | F | F | F | F |
| 94. | Jan 21 | Jan 2 | F | M | M | M | M | M | N/A | M |
| 95. | Dec 13 | Dec 2 | F | F | F | F | F | F | N/A | F |

TABLE 3-continued

Results of gender-determining assay

| Subject No. | E.D.D.* | A.D.D.+ | Wk 12 | Wk 14 | Wk 16 | Wk 18 | Wk 20 | Wk 22 | Ultra Sound | Actual |
|---|---|---|---|---|---|---|---|---|---|---|
| 96. | Jan 12 | Jan 17 | F | F | F | F | F | F | N/A | F |
| 97. | Feb 24 | Feb 25 | F | F | F | F | F | F | N/A | F |
| 98. | Mar 8 | Mar 15 | M | M | M | M | M | M | F | M |
| 99. | Apr 20 | May 1 | F | F | F | F | F | F | N/A | F |
| 100. | May 15 | Apr 30 | F | M | M | M | M | M | N/A | M |
| 101. | May 23 | May 11 | M | M | M | M | M | M | N/A | M |
| 102. | May 4 | May 11 | F | F | F | F | F | F | F | F |
| 103. | May 12 | May 14 | F | F | F | F | F | F | N/A | F |

*Estimated Delivery Date (E.D.D.)
+Actual Delivery Date (A.D.D.)

What is claimed is:

1. A kit for determining an unborn child's gender from pregnant woman's urine, comprising a unit dose of a gender-indicating composition which comprises thymol blue and at least one of a male child color standard and a female child color standard; and wherein the male child color standard is red to orange and the female child color standard is blue to green.

2. The kit of claim 1, wherein the gender-indicating composition further comprises bromthymol blue.

3. The kit of claim 1, wherein the gender-indicating composition further comprises a neutral water-miscible organic solvent.

4. The kit of claim 2, wherein the neutral water-miscible organic solvent includes dimethylformamide, dimethylacetamide, dimethylsulfoxide, acetone, methyl ethyl ketone, n-methyl pyrrolidone, acetonitrile, water-miscible alcohol or a mixture thereof.

5. The kit of claim 4, wherein the alcohol comprises ethylene glycol, methanol, ethanol, isopropanol, or a mixture thereof.

6. The kit of claim 4, wherein the alcohol comprises methanol.

7. The kit of claim 1, wherein the gender-indicating composition is a solution which includes about 0.1 ppm to about 50 ppm thymol blue.

8. The kit of claim 7, wherein the solution further comprises about 0.1 ppm to about 50 ppm bromthymol blue.

9. The kit of claim 1, further comprising instructions for performing the colorimetric assay.

10. The kit of claim 1, wherein the gender-indicating composition further comprises bromthymol blue, phenolphthalin, methyl red or a mixture thereof.

* * * * *

UNITED STATES PATENT AND TRADEMARK OFFICE
CERTIFICATE OF CORRECTION

PATENT NO.      : 6,420,182 B1
DATED           : July 16, 2002
INVENTOR(S)     : Start It is certified that error appears in the above-identified patent and that said Letters Patent is hereby corrected as shown below:

Column 5,
Lines 18 and 41, "calorimetric" should read -- colorimetric --

Column 6,
Line 29, "be -glass" should read -- glass --
Line 38, "calorimetric" should read -- colorimetric --

Column 9,
Line 32, "claim 2" should read -- claim 3 --

Signed and Sealed this

Third Day of December, 2002

JAMES E. ROGAN
*Director of the United States Patent and Trademark Office*